United States Patent [19]
Oda et al.

[11] 3,933,931
[45] Jan. 20, 1976

[54] PROCESS FOR PREPARING PERFLUOROALKYL IODIDES

[75] Inventors: Yoshio Oda; Manabu Suhara, both of Yokohama, Japan

[73] Assignee: Asahi Glass Co., Ltd., Tokyo, Japan

[22] Filed: Oct. 8, 1971

[21] Appl. No.: 187,867

[30] Foreign Application Priority Data
Oct. 9, 1970   Japan.................. 45-88337

[52] U.S. Cl. ................ 260/653; 252/432; 252/441
[51] Int. Cl.² .................. C07C 17/04; C07C 19/07
[58] Field of Search ..................... 260/653

[56] References Cited
UNITED STATES PATENTS
3,821,321   6/1974   Hellberg et al. .................. 260/653

*Primary Examiner*—D. Horwitz
*Attorney, Agent, or Firm*—Oblon, Fisher, Spivak, McClelland & Maier

[57] ABSTRACT

Perfluoroaklyl iodides are prepared by reacting iodine, iodine pentafluoride and tetrafluoroethylene in the presence of a fluoride catalyst selected from the group consisting of niobium fluoride, tantalum fluoride, boron fluoride, and molybdenum fluoride.

11 Claims, No Drawings

PROCESS FOR PREPARING PERFLUOROALKYL IODIDES

BACKGROUND OF THE INVENTION

1. Field of the Invention:

This invention relates to a process for preparing perfluoroalkyl iodides, and more particularly to a new and improved process for preparing perfluoroalkyl iodides by reacting iodine, iodine pentafluoride and tetrafluoroethylene in the presence of a novel fluoride catalyst.

2. Description of the Prior Art:

It is known that perfluoroalkyl iodides can be prepared by the reaction of tetrafluoroethylene with iodine and iodine pentafluoride, and the prior art describes various catalysts which may be used for promoting such a reaction. British Pat. Specification No. 930,758 (corresponding to U.S. Pat. No. 3,006,973), for instance discloses that the metals aluminum, magnesium, thorium, beryllium, calcium, strontium, or the iodides thereof, can be used as catalysts for this reaction and U.S. Pat. No. 3,132,185 (corresponding to British Pat. No. 998,235) discloses that antimony pentafluoride, antimony trifluoride, or anhydrous stannous fluoride may be used to promote this reaction. None of the prior art processes, however, are entirely satisfactory, because the yield of the perfluoroalkyl iodides obtained is low, unless antimony catalysts are used, but these catalysts are difficulty to handle and hence, are not satisfactory from an industrial point of view.

SUMMARY OF THE INVENTION

It has now been found that perfluoroalkyl iodides can be prepared in exceptionally high yields by the use of certain metal fluorides, including niobium fluoride, tantalum fluoride, boron fluoride, and molybdenum fluoride, in the reaction of tetrafluoroethylene with iodine and iodine pentafluoride. These catalysts are capable of attaining exceptionally high yields with essentially no undesirable side reactions. Moreover, they are safer and provide a higher reaction rate, than the conventional catalysts described in the prior art.

In the process of the present invention, iodine and iodine pentafluoride are introduced into a closed reactor system together with an effective amount of the catalyst. Tetrafluoroethylene is also fed into the reactor, and, if the reaction is not self-initiating, the contents are gently heated. Since the reaction is exothermic, however, once, it is initiated, it will be self-sustaining without the need for additional heat.

The reaction temperature should be maintained within the range of 0°C to 150°C, and the reaction is preferably carried out under autogeneous pressure.

The perfluoroalkyl iodides prepared according to the present invention may be used directly without further purification as telogens for the production of telomers according to such known processes, as thermic telomerization, telomerization catalyzed by peroxides or by actinic radiation. The perfluoroethyl iodide prepared according to the present invention, for example, can be used to produce perfluoroalkyl iodides of the formula $C_2F_5(C_2F_4)_nI$ by telomerization with tetrafluoroethylene. They are also important raw materials for providing perfluorocarbonaceous molecules having chemical functional groups. The longer chain perfluoroalkyl iodides may be converted to perfluoro acids, which are well-known surface-active agents.

DETAILED DESCRIPTION OF THE PREFERRED EMBODIMENTS

The reaction of the present invention, proceeds as follows:

$$5C_2F_4 + II_2 + IF_5 \rightarrow 5C_2F_5I$$

In this reaction, the mixture of iodine and iodine pentafluoride should be used in a molar ratio of $I_2 : IF_5$ of at least 1 : 1. The upper limit of the $I_2 : IF_5$ molar ratio is not critical, but from a practical stand point, it should not exceed 5 : 1. Best results are generally obtained, when the $I_2 : IF_5$ molar ratio is in the range of from 1.8 : 1 to 2.5 : 1, the optimum ratio being approximately 2 : 1. When this molar ratio is at least 2 : 1, the tetrafluoroethylene should be used in an amount of at least 5 moles for each mole of $IF_5$. Excess tetrafluoroethylene may be used, but the reaction will stop after the 5 moles of the tetrafluoroethylene have been reacted. Moreover, excess tetrafluoroethylene will be lost, if excess iodine is present. Generally, the molar ratio of tetrafluoroethylene to iodine pentafluoride is not critical, although it is preferred to employ a stoichiometric excess of tetrafluoroethylene. The tetrafluoroethylene: iodine pentafluoride molar ratio, should generally be in the range of from 3 : 1 to 10 : 1 and preferably in the range of from 5 : 1 to 8 : 1.

The end products prepared in the reaction according to the present invention are dependent upon the molar ratio of iodine to iodine pentafluoride. When the $I_2 : IF_5$ ratio is at least 2 : 1, the end product of the reaction will be essentially perfluoroethyl iodine. If the molar ratio of $I_2 : IF_5$ is less than 2 : 1, products of the formula $C_2F_5(CF_2CF_2)_nI$ may also be produced, usually in conjunction with varying amounts of $C_2F_5I$, depending on the $I_2 : IF_5$ ratio and the amount of tetrafluoroethylene used.

Products having the formula $C_2F_5(CF_2CF_2)_nI$ are produced as mixtures, and therefore there may be several values for n in the same reaction product.

The particular value of N and the number of products obtained having the formula $C_2F_5(CF_2CF_2)_nI$ will vary depending upon the amount of tetrafluoroethylene used. Almost any amount of tetrafluoroethylene will provide some product.

The selection of the molar ratio of tetrafluoroethylene to $IF_5$ is governed by the molecular weight desired in the end products.

It has now been found that the most effective catalysts are niobium fluoride, tantalum fluoride, boron fluoride, titanium fluoride, molybdenum fluoride or tungsten fluoride. It is also possible to use metallic niobium, metallic tantalum, or molybdenum or others which are convertible to the fluorides, as the catalyst, in the reaction system. Moreover, combinations of two or more of the catalysts may be used, or combinations of any of these catalysts with a conventional catalyst, may be used, so far as the conventional catalyst does not adversely affect the functioning of the primary catalyst. Since the niobium fluoride and tantalum fluoride will provide high reaction rates, it is possible to attain a high degree of conversion in a short period of time and a high selectivity of the reaction toward the intended product, perfluoroalkyl iodide. Moreover, it is possible to reuse these fluoride catalysts without significant loss in their catalytic activity.

Since both niobium fluoride and tantalum fluoride are effective in smaller amounts than any of the boron fluoride or molybdenum fluoride, it is preferable to use either the niobium fluoride or the tantalum fluoride.

If niobium, tantalum, or molybdenum is added in the form of metal to the reaction system, it will be reacted with $IF_5$ to yield the desired metal fluoride. Accordingly, separate synthesis of these fluoride catalysts may be eliminated and difficulties which might otherwise occur during synthesis can be advantageously minimized. It is therefore, advantageous to use the metal per se for catalyzing the reaction.

The concentration of the catalyst is not critical. They can effectively be used in very small amounts, e.g., 0.0005 moles per mole of $IF_5$, or in larger amounts, e.g., up to 0.3 moles per mole of $IF_5$. Usually, the catalyst will be used in amounts ranging from 0.001 to 0.2 mole for each mole of $IF_5$. Preferably the catalyst should be used within the range of from 0.003 to 0.1 mole per mole of $IF_5$.

The reaction of the present invention will occur at relatively low temperatures, as low as − 20°C. Furthermore, higher temperatures, however, even as high as 200°C are possible. For practical considerations, however, the reaction is preferably carried out at a temperature within the range of between 0°C and 150°C. The preferred reaction temperature in the present invention will lie within the range of from 10° to 100°C, particularly from 40° to 80°C.

The reaction pressure is not critical. The reaction may be conducted at atmospheric pressure, although in many cases the reactants will be volatile at the reaction temperature used so that it will be desirable to conduct the reaction under moderate superatmospheric pressures, ranging for example, from 3 to 50 atms. depending upon the pressure autogeneously developed during the reaction. Higher pressures, however, up to any practical limit, e.g., 200 atms. may be used.

Reaction time is not critical. The usual reaction period to obtain a reasonable to good conversion, will generally be from about one to thirty hours.

The procedure for carrying out the present invention is relatively simple. For example, iodine, iodine pentafluoride, and the catalyst may be placed in an agitated pressure vessel and heated to the reaction temperature. The reaction vessel should also be equipped with means for cooling the reaction mixture. The tetrafluoroethylene should be added slowly, since the reaction is rather exothermic and a considerable temperature rise may occur. If tetrafluoroethylene is added, either in bulk initially or too rapidly during the reaction, the process may become uncontrollable. The rate of tetrafluoroethylene addition is controlled mainly by the ability of the reaction equipment used to remove heat from the reaction mixture. It is also desirable to keep the temperature as low as possible, since iodine pentafluoride tends to be much more corrosive at higher temperatures. When a small proportion of tetrafluoroethylene is added to the iodine, iodine pentafluoride mixture, there is usually an almost immediate release of heat. The pressure due to the added tetrafluoroethylene will decrease as it is consumed. After the added tetrafluoroethylene has reacted, additional increments are introduced until the desired amount of tetrafluoroethylene has been added. Alternatively, the tetrafluoroethylene may be added slowly, in a continuous manner, at a rate such that the reaction temperature is maintained approximately constant, by removing heat from the reaction.

All of the materials used in the process of the present invention are commercially available materials. The iodine pentafluoride can be conveniently formed in situ in the mixing vessel by charging solid iodine into the vessel and introducing fluorine gas through the inlet tube to produce liquid $IF_5$. This product may include unreacted iodine. The preparation of iodine pentafluoride is described in a review article by Booth and Pinkston, Chem. Rev., vol. 41, page 421 (1947), or in the U.S. Pat. No. 3,367,745.

Iodine pentafluoride is very corrosive, particularly to metals, if the anhydrous condition is not maintained. Under anhydrous conditions, corrosion is not severe and metals, such as stainless steel, "Hastelloy-C" (trade mark), "Inconel" (trade mark), and ordinary steel, can be used in forming the reaction equipment. Steel is more severely attacked than the others, but not enough to prevent its use.

In the process according to the present invention, the reaction of tetrafluoroethylene with iodine and iodine pentafluoride may be carried out in a liquid inert medium. The medium employed according to the process of the invention may be any solvent which is inert to the reactants, the reaction products, and the equipment utilized. Perfluoroethyl iodide is the preferred solvent, since it is also one of the principal reactants.

In the process according to the present invention, the perfluoroethyl iodide, employed as an inert medium, may be added in amounts ranging from 0.5 to 20 parts by weight per part by weight of iodine pentafluoride.

Preferably, the medium is used in amounts of from 2 to 10 parts by weight for each part of iodine pentafluoride. The perfluoroethyl iodide medium may be introduced into the reaction vessel by any suitable procedure known in the art. For example, the perfluoroethyl iodide produced according to the process of the present invention may be circulated into the reaction vessel as the medium.

Prior to reaction with tetrafluoroethylene, it is preferable to let the mixture of iodine, iodine pentafluoride and catalyst remain in contact with one another for several hours, preferably while maintaining the mixture at an elevated temperature, ranging up to about 200°C. Usually, heating the mixture between temperatures of 100°C and 200°C for a period of 0.5 to 24 hours will give optimum results. Where a liquid inert medium is employed, such as perfluoroethyl iodide, it is preferred to conduct the pre-heating of the mixture of iodine, iodine pentafluoride and catalyst in the presence of the inert medium. Apparently, the activity of the catalyst is improved by such pre-heating in the presence of the medium, since more reproducible results are obtainable, and generally higher yields and conversions result by this procedure.

Where a liquid inert medium is employed, it is preferred to conduct the pre-heating of the mixture between temperatures of 100°C and 200°C for a period of 0.5 to 24 hours, particularly between temperatures of 110°C and 140°C for a period of 1 to 12 hours.

For a clearer understanding of the invention, the following specific examples are given. These examples are intended to be merely illustrative of the invention and not in limitation thereof. Unless otherwise specified, all parts are by weight.

EXAMPLE 1

A 0.1 litre stainless steel autoclave was charged with 16.8 grams (66 millimoles) of iodine, 7.3 grams (33 millimoles) of iodine pentafluoride and 25 milligrams (0.27 millimoles) of granular metallic niobium. The autoclave was sealed and cooled to — 60°C, evacuated to remove air, and then heated at 75°C with agitation. 19.3 grams (193 millimoles) of tetrafluoroethylene was added intermittently, with agitation, to the autoclave, and the temperature was maintained at approximately 75°C and the pressure between 4 and 12 kgs/cm$^2$ gauge for 1.5 hours.

At the end of the reaction, 39.0 grams (159 millimoles) of $C_2F_5I$ was obtained. The selectivity of $C_2F_5I$ was 99% based on the quantity of tetrafluoroethylene consumed. The yield of $C_2F_5I$ was 96% based on $IF_5$ used.

In Examples 2 to 4 and References 1 to 5, Example 1 was repeated except using different types of catalysts as stated in the following table:

| | Catalyst | Amount of Cat. (g) | Reaction period (hr) | Yield of $C_2F_5I$(%) |
|---|---|---|---|---|
| Example 2 | Nb | 0.10 | 2.0 | 97 |
| Example 3 | NbF$_5$ | 0.10 | 2.0 | 97 |
| Example 4 | Ta | 0.10 | 1.5 | 98 |
| Reference 1 | Bi-BiF$_3$ | 0.10 | 5.5 | 35 |
| Reference 2 | AgF | 0.10 | 8.0 | 53 |
| Reference 3 | CaF$_2$ | 0.10 | 4.5 | 34 |
| Reference 4 | AlF$_3$ | 0.10 | 6.7 | 66 |
| Reference 5 | None | — | 3.5 | 35 |

Comparative Example

A 0.1 litre stainless steel autoclave was charged with 16.8 g (66 millimoles) of iodine, 7.3 g (33 millimoles) of iodine pentafluoride, and 100 mg (2.1 millimoles) of granular metallic titanium. The autoclave was sealed and cooled to — 60°C, and evacuated to remove air and then heated at 75°C.

18.2 g (182 millimoles) of tetrafluoroethylene was intermittently added to the autoclave while stirring, and was then reacted at about 75°C for 4.5 hours under a gauge pressure of 4–12 kg/cm$^2$.

After the reaction, the contents were separated to yield 36.4 g (148 millimoles) of $C_2F_5I$. The selectivity of $C_2F_5I$ based on $C_2F_4$ was 100% and the yield of $C_2F_5I$ based on $IF_5$ was 95%.

EXAMPLE 5

The process of Example 5 was repeated except using different types of catalyst.

The results are summarized in Table 2.

TABLE 2

| | Catalyst | Amount of Cat. (g) | Reaction period (hr) | $C_2F_5I$ yield % (based on $IF_5$) |
|---|---|---|---|---|
| Example 6 | BF$_3$ | 0.36 | 4.5 | 91 |

EXAMPLE 6

A 0.1 litre stainless autoclave was charged with 16.8 g (66 millimoles) of iodine, 7.4 g (33 millimoles) of iodine pentafluoride, and 100 g (1.0 millimole) of granules of metallic molybdenum.

The autoclave was sealed, evacuated, and cooled to — 60°C. 19.5 g (195 millimoles) of $C_2F_4$ was then intermittently added to the autoclave at 75°C and was reacted under a gauge pressure of 4–12 kg/cm$^2$ for 2.3 hours.

After the reaction, the contents were separated, to yield 38.3 g (156 millimoles) of $C_2F_5I$ based on $C_2F_4$ was 99% and the yield of $C_2F_5I$ based on $IF_5$ was 93%.

EXAMPLE 7

The process of Example 1 was repeated except using 13 milligrams of metallic niobium and reacting for 2.5 hours.

The yield of $C_2F_5I$ based on $IF_5$ was 93%.

EXAMPLE 8

A 0.1 litre stainless steel autoclave was charged with 16.8 g (66 millimoles) of iodine, 7.3 g (33 millimoles) of iodine pentafluoride, and 43.8 g (178 millimoles) of perfluoroethyl iodide and 0.050 g (0.53 millimoles) of metallic niobium. The autoclave was sealed and was kept at 120°C for 1 hour while stirring. 18.2 g (182 millimoles) of tetrafluoroethylene was then added to the autoclave at 75°C, and was reacted under a gauge pressure of 5–12 kg/cm$^2$ for 1.5 hours. After the reaction, the contents were separated to yield 83.4 g (339 millimoles) of $C_2F_5I$.

The yield of $C_2F_5I$ based on $IF_5$ was 98%.

EXAMPLE 9

After the reaction of Example 2, $C_2F_5I$ was separated from the reaction mixture, and 16.8 g of iodine and 7.3 g of $IF_5$ were added to 0.5 g of residue containing niobium fluoride and a small amount of iodine.

The reaction of Example 10 was then further conducted for 1.5 hours.

As a result, the yield of $C_2F_5I$ based on $IF_5$ was 94%. This example shows the reusability of the catalyst of this invention.

EXAMPLE 10

A 0.1 litre stainless steel autoclave was charged with 16.8 g (66 millimoles) of iodine, 7.3 g (33 millimoles) of iodine pentafluoride and 0.10 g (0.55 millimoles) of metallic tantalum. The autoclave was sealed and was kept at 118°C for 2 hours while stirring. 18.5 g (185 millimoles) of tetrafluoroethylene was then intermittently charged at 75°C, and was reacted under the gauge pressure of 5–12 kg/cm$^2$ for 2 hours. After the reaction, the content was separated to yield 64.2 g (261 millimoles) of $C_2F_5I$. The yield of $C_2F_5I$ based on $IF_5$ was 41%.

Having now fully described the invention, it will be apparent to one of ordinary skill in the art that many changes and modifications can be made thereto without departing from the spirit or scope of the invention.

What is claimed and desired to be secured by Letters Patent of the United States is:

1. A process for preparing perfluoroethyl iodide by the reaction of iodine, iodine pentafluoride and tetrafluoroethylene, in which the molar ratio of iodine to iodine pentafluoride is at least 1 : 1 and the molar ratio of tetrafluoroethylene to iodine pentafluoride is at least 3 : 1 and the reaction is carried out in the presence of a catalyst selected from the group consisting of niobium fluoride, tantalum fluoride, boron fluoride, and molybdenum fluoride and at a temperature of from 0°C to 150°C. and a pressure of from atmospheric pressure to 200 atmospheres, and wherein said reaction is carried out in the liquid phase in a liquid inert medium wherein liquid iodine pentafluoride or perfluoroalkyl iodide and catalysts are first introduced into the reaction zone and then tetrafluoroethylene is added.

2. A process according to claim 1, in which the reaction is carried out at a temperature of from 40° to 80°C.

3. A process according to claim 1, in which the reaction is carried out under autogenous pressure.

4. A process according to claim 1, in which the catalyst is present in the amount of from 0.001 to 0.2 moles per mole of iodine pentafluoride.

5. A process according to claim 1, in which the catalyst is niobium fluoride or tantalum fluoride.

6. A process according to claim 1, in which the molar ratio of $I_2 : IF_5$ is in the range of from 1.8 : 1 to 2.5 : 1.

7. A process according to claim 1, in which the molar ratio of tetrafluoroethylene : iodine pentafluoride is in the range of from 5 : 1 to 7 : 1.

8. A process according to claim 1, in which the reaction is carried out in a liquid inert medium.

9. A process according to claim 1 wherein the reaction is carried out in perfluoroethyl iodide.

10. A process according to claim 9, in which the perfluoroethyl iodide medium is used in amounts ranging from 0.5 to 20 parts by weight per part of iodine pentafluoride.

11. A process according to claim 9, in which the mixture of iodine, iodine pentafluoride, catalyst and perfluoroethyl iodide medium is pre-heated between temperatures of 100°C and 200°C for a period of 0.5 to 24 hours prior to reaction with tetrafluoroethylene.

* * * * *